(12) United States Patent
Broderick et al.

(10) Patent No.: US 9,416,071 B2
(45) Date of Patent: Aug. 16, 2016

(54) HYDROCARBON CONVERSION PROCESSES USING LACTAMIUM-BASED IONIC LIQUIDS

(71) Applicant: UOP LLC, Des Plaines, IL (US)

(72) Inventors: Erin M. Broderick, Arlington Heights, IL (US); Stuart Smith, Lake Zurich, IL (US); Alakananda Bhattacharyya, Glen Ellyn, IL (US); Susie C. Martins, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 64 days.

(21) Appl. No.: 14/556,932

(22) Filed: Dec. 1, 2014

(65) Prior Publication Data

US 2015/0321977 A1 Nov. 12, 2015

Related U.S. Application Data

(60) Provisional application No. 61/989,441, filed on May 6, 2014.

(51) Int. Cl.

| | |
|---|---|
| *C07C 2/26* | (2006.01) |
| *C07C 6/08* | (2006.01) |
| *C07C 2/58* | (2006.01) |
| *C07C 6/10* | (2006.01) |
| *C07C 5/27* | (2006.01) |
| *C07C 2/62* | (2006.01) |
| *C07C 2/22* | (2006.01) |

(Continued)

(52) U.S. Cl.
CPC ... *C07C 6/10* (2013.01); *C07C 2/20* (2013.01); *C07C 2/22* (2013.01); *C07C 2/60* (2013.01); *C07C 2/62* (2013.01); *C07C 5/2727* (2013.01); *C07C 5/2748* (2013.01); *C07C 6/123* (2013.01); *C07C 2531/02* (2013.01); *C07C 2531/14* (2013.01)

(58) Field of Classification Search
CPC .......... C07C 6/10; C07C 5/2727; C07C 2/22; C07C 2/62; C07C 2351/14
USPC .......................................... 585/511, 708, 727
See application file for complete search history.

(56) References Cited

U.S. PATENT DOCUMENTS

| | | | |
|---|---|---|---|
| 3,155,642 A | 11/1964 | Duck et al. | |
| 3,170,904 A | 2/1965 | Ueda et al. | |

(Continued)

FOREIGN PATENT DOCUMENTS

| | | |
|---|---|---|
| CN | 1852898 A | 10/2006 |
| CN | 1943872 A | 4/2007 |

(Continued)

OTHER PUBLICATIONS

Du et al., "Investigation of Physicochemical Properties of Lactam-Based Bronsted Acidic Ionic Liquids," Journal of Physical Chemistry B (2005), 109 (41), 19542-19546.

(Continued)

*Primary Examiner* — William Cheung

(57) ABSTRACT

A hydrocarbon conversion process is described. The process involves contacting a hydrocarbon feed with a lactamium based ionic liquid catalyst in a reaction zone under reaction conditions to form a mixture comprising reaction products, and the lactamium based ionic liquid catalyst. Typical hydrocarbon conversion processes include alkylation, oligomerization, isomerization, disproportionation, and reverse disproportionation.

20 Claims, 1 Drawing Sheet

(51) Int. Cl.
*C07C 2/20* (2006.01)
*C07C 2/60* (2006.01)
*C07C 6/12* (2006.01)

(56) References Cited

U.S. PATENT DOCUMENTS

| | | |
|---|---|---|
| 3,170,906 A | 2/1965 | Ueda at al. |
| 3,457,321 A | 7/1969 | Hambling et al. |
| 3,483,268 A | 12/1969 | Hambling at al. |
| 3,483,269 A | 12/1969 | Magoon at al. |
| 3,505,425 A | 4/1970 | Jones et al. |
| 3,562,351 A | 2/1971 | Mertzweiller at al. |
| 3,592,869 A | 7/1971 | Cannell |
| 3,644,564 A | 2/1972 | van Zwet at al. |
| 3,663,451 A | 5/1972 | Hill |
| 3,679,772 A | 7/1972 | Yoo |
| 3,697,617 A | 10/1972 | Yoo et al. |
| 3,755,490 A | 8/1973 | You et al. |
| 3,954,668 A | 5/1976 | Yoo et al. |
| 3,981,941 A | 9/1976 | Butter |
| 4,520,221 A | 5/1985 | Hsia Chen |
| 4,547,613 A | 10/1985 | Garwood et al. |
| 4,642,404 A | 2/1987 | Shihabi |
| 4,757,042 A | 7/1988 | Threlkel |
| 4,764,440 A | 8/1988 | Jones et al. |
| 5,104,840 A | 4/1992 | Chauvin et al. |
| 5,284,989 A | 2/1994 | Apelian et al. |
| 5,824,832 A | 10/1998 | Sherif et al. |
| 5,895,830 A | 4/1999 | Stine et al. |
| 7,053,261 B2 | 5/2006 | Herbst et al. |
| 7,220,869 B2 * | 5/2007 | Deng ............ B01J 31/0282 540/485 |
| 7,285,698 B2 | 10/2007 | Liu et al. |
| 9,233,928 B2 * | 1/2016 | Broderick ............ C07D 223/10 |
| 2004/0059173 A1 | 3/2004 | Houzvicka et al. |
| 2004/0133056 A1 | 7/2004 | Liu et al. |
| 2006/0135839 A1 | 6/2006 | Elomari et al. |
| 2007/0021604 A1 | 1/2007 | Deng et al. |
| 2007/0142676 A1 | 6/2007 | Elomari et al. |
| 2007/0225538 A1 | 9/2007 | Elomari |
| 2013/0248423 A1 | 9/2013 | Serban et al. |

FOREIGN PATENT DOCUMENTS

| | | |
|---|---|---|
| CN | 1978431 A | 6/2007 |
| CN | 1978434 A | 6/2007 |
| CN | 101985435 A | 3/2011 |
| EP | 2 520 558 A1 * | 11/2012 |
| EP | 2520558 A1 | 11/2012 |
| GB | 1123474 | 8/1968 |

OTHER PUBLICATIONS

Jiang et al., "Thermodynamic Properties of Caprolactam Ionic Liquids," Chinese Journal of Chemical Engineering (2013), 21(7), 766-769.

Yang et al., "Novel Ionic Liquid Crystals Based on N-Alkylcaprolactam as Cations," Chemistry Materials (2007), 19(10), 2544-2550.

Fabos et al., "e-Caprolactamium Hydrogen Sulfate: An Ionic Liquid Used for Decades . . . " ChemSusChem (2008), 1(3), 189-192.

Guo et al., "Clean Beckmann rearrangement of cyclohexanone oxime in caprolactam-based Bronsted acidic ionic liquids", Green Chemistry (2006), vol. 8, 296-300.

Guo et al., "Absorption and Oxidation of H2S in Caprolactam Tetrabutyl Ammonium Bromide Ionic Liquid," Energy & Fuels (2011), vol. 25, 159-161.

* cited by examiner

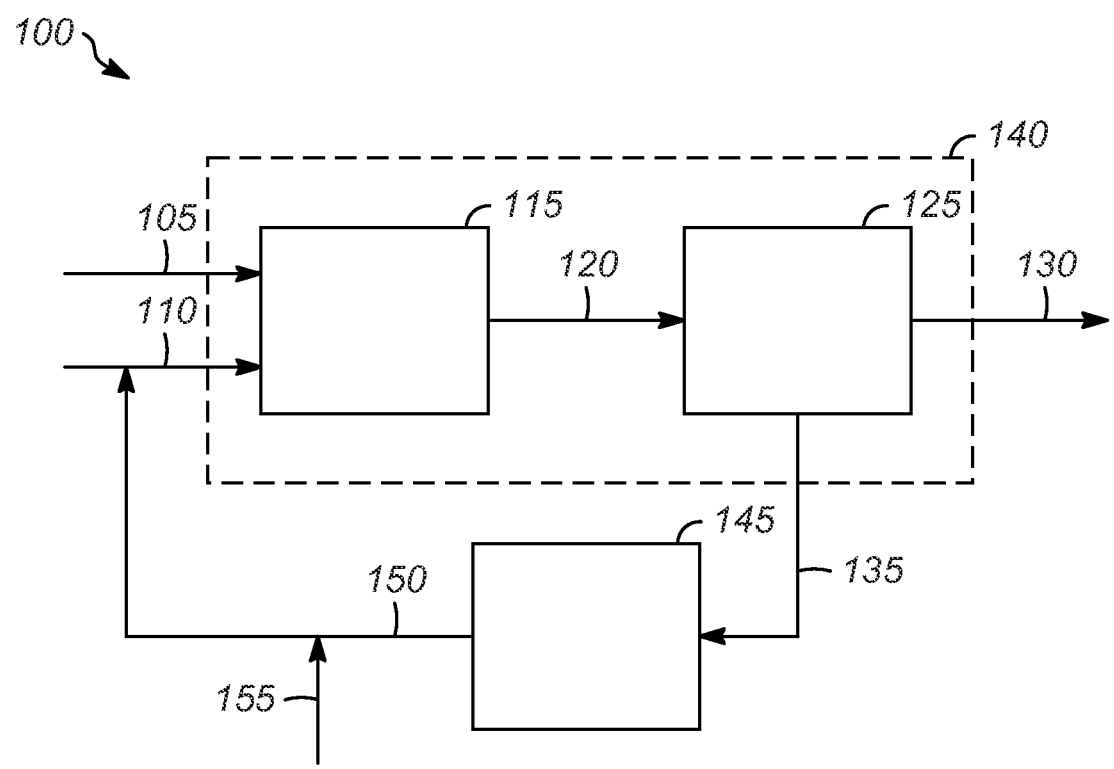

HYDROCARBON CONVERSION PROCESSES USING LACTAMIUM-BASED IONIC LIQUIDS

This application claims the benefit of Provisional Application Ser. No. 61/989,441 filed May 6, 2014, entitled Hydrocarbon Conversion Processes Using Lactamium-Based Ionic Liquids.

BACKGROUND OF THE INVENTION

There are a variety of hydrocarbon conversion processes, and these processes utilize different catalysts.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Solid catalysts are also used for alkylation. However, solid catalysts are generally rapidly deactivated by the presence of water, which may be present in the feed.

Processes for the oligomerization of light olefins (e.g. ethylene, propylene, and butylene) to produce higher carbon number olefin products (e.g. $C_{6+}$ olefins) are well known.

Oligomerization processes have been employed to produce high quality motor fuel components as well as petrochemicals from ethylene, propylene, and butylene. These oligomerization processes are also referred to as catalytic condensation and polymerization, with the resulting motor fuel often referred to as polymer gasoline. In the refining area, methods have been continually sought to improve the octane number of the gasoline boiling range oligomerization products. This octane enhancement is generally realized through the improvement of the oligomerization reaction selectivity to enhance the representation of high octane blending components (e.g., branched olefins) in the product slate. The ability of the process to better target specific carbon number species is also a primary consideration when highly purified chemical grade products are desired. In any case, the enrichment of product slate to the targeted species, in addition to providing a higher quality and quantity of useable products, also benefits catalyst life. This is due to the reduction in non-selective heavy oligomers that condense into coke which ultimately covers the catalyst.

Known catalysts for effecting the oligomerization reaction include heterogeneous catalysts such as solid acids and homogeneous catalysts, in particular boron trifluoride as described, for example, in U.S. Pat. No. 3,981,941. Other catalysts fall within the description of mild protonic acids, generally having a Hammett acidity function of less than −5.0. Particularly preferred among these are solid phosphoric acid (SPA) catalysts having as a principal ingredient an acid of phosphorous such as ortho, pyro, or tetraphosphoric acid. Details of SPA catalysts are provided in the prior art, for example in U.S. Pat. No. 5,895,830. The use of zeolites as oligomerization catalysts is also described, along with various catalyst treatment methods designed to improve performance in U.S. Pat. Nos. 4,547,613, 4,520,221, 4,642,404, and 5,284,989, for example. Another type of catalyst which may be employed comprises a supported metal compound, as described in U.S. Pat. Nos. 3,562,351, 3,483,269, 3,592,869 3,644,564, 3,679,772, 3,697,617, 3,663,451, 3,755,490, 3,954,668, 3,170,904, 3,170,906. Unsupported metal catalysts are described in Japanese Patent 5024282, Japanese Patent 4722206, U.S. Pat. Nos. 3,155,642, 3,155,642, 3,457,321, 3,483,268, and 3,505,425, and British Patent 1,123,474. U.S. Pat. No. 4,757,042 describes a catalyst comprising a complex of nickel or palladium, certain fluoro-organo sulfur ligands and an organo-metallic reducing agent.

The disproportionation of paraffins (e.g., isopentane ($iC_5$)) involves reacting two moles of hydrocarbon to form one mole each of two different products, one having a carbon count greater than the starting material and the other having a carbon count less than the starting material. The total number of moles in the system remains the same throughout the process, but the products have different carbon counts from the reactants.

Suitable catalysts include, but are not limited to, HF, sulfated zirconias, $AlCl_2/SiO_2$, zeolites, ionic solids, platinum on chlorided $Al_2O_3/Ga_2O_3$ supports, supported ionic liquids, $Pt/W/Al_2O_3$, $HF/TiF_4$, or combinations thereof.

Isomerization of linear paraffins to their branched isomers increases their octane number and thus their value to a refiner. Isomerization processes involve reacting one mole of a hydrocarbon (e.g., normal pentane) to form one mole of an isomer of that specific hydrocarbon (e.g., isopentane). The total number of moles remains the same throughout this process, and the product has the same number of carbons as the reactant.

Current isomerization processes use chlorided alumina, sulfated zirconia, or zeolites in conjunction with platinum. Process temperatures range from about 120° C. for chlorided alumina up to about 260° C. for zeolite type catalysts. These reactions are run at temperatures which allow the feed to reach equilibrium. At lower temperatures, the equilibrium favors the branched isomers possessing the higher octane number.

Acidic ionic liquids can be used as an alternative to the commonly used strong acid catalysts in hydrocarbon conversion processes. Ionic liquids are catalysts that can be used in a variety of catalytic reactions, including the alkylation of paraffins with olefins. Ionic liquids are salts comprised of cations and anions which typically melt below about 100° C.

Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

Although ionic liquid catalysts can be very active, alkylation reactions need to be run at low temperatures, typically between −10° C. to 0° C., to maximize the alkylate quality. This requires cooling the reactor and reactor feeds, which adds substantial cost to an alkylation process utilizing ionic liquids in the form of additional equipment and energy. The most common ionic liquid catalyst precursors for alkylation include imidazolium, or pyridinium-based cations coupled with the chloroaluminate anion ($Al_2Cl_7^-$).

Isomerization processes utilizing ionic liquid catalysts have been developed, such as, US 2004/059173, and U.S. Pat. No. 7,053,261, for example.

Ionic liquids provide advantages over other catalysts, including being less corrosive than catalysts like HF, and being non-volatile.

However, the cost of ionic liquids has limited the widespread adoption of ionic liquids.

There is a need for lower cost ionic liquids for use in a variety of hydrocarbon conversion processes.

SUMMARY OF THE INVENTION

One aspect of the present invention is a hydrocarbon conversion process. In one embodiment, the process involves contacting a hydrocarbon feed with a lactamium based ionic liquid catalyst in a reaction zone under reaction conditions to form a mixture comprising reaction products, and the lactamium based ionic liquid catalyst.

BRIEF DESCRIPTION OF THE DRAWING

The FIGURE illustrates one embodiment of a hydrocarbon conversion process.

DETAILED DESCRIPTION OF THE INVENTION

The present invention involves the use of lactamium based ionic liquids as catalysts for hydrocarbon conversion processes, including, but not limited to, alkylation, oligomerization, isomerization, disproportionation, and reverse disproportionation. It was unexpectedly found that the oxygen in the lactam did not interact with the aluminum of the anion in a way that inhibited the performance of the catalyst.

A hydrocarbon feed is contacted with the lactamium based ionic liquid in a reaction zone. The reaction zone is under the appropriate conditions for the particular hydrocarbon conversion involved. A mixture is formed including the reaction products, and the lactamium based ionic liquid.

The reaction products can be separated from the lactamium based ionic liquid catalyst, which can then be regenerated using a suitable regeneration process. The regenerated lactamium based ionic liquid catalyst can be recycled to the reaction zone.

The FIGURE illustrates one embodiment of a hydrocarbon conversion process 100 of the present invention. Hydrocarbon feed 105 and lactamium based ionic liquid 110 enter hydrocarbon conversion zone 115. The lactamium based ionic liquid 110 catalyzes the hydrocarbon conversion reaction. The effluent 120 from the hydrocarbon conversion zone 115 includes the reaction products of the hydrocarbon conversion reaction and the lactamium based ionic liquid. The effluent 120 is sent to separation zone 125 where the reaction products 130 are separated from the lactamium based ionic liquid 135. In some embodiments, the hydrocarbon conversion zone 115 and the separation zone 125 are in separate vessels. In other embodiments, they are in the same vessel 140.

The lactamium based ionic liquid 135 can be recycled to the hydrocarbon conversion zone 115. The lactamium based ionic liquid 135 can be sent to a regeneration zone 145 for regeneration if needed. The regenerated lactamium based ionic liquid 150 can be reactivated with an acid 155 if needed. The regenerated lactamium based ionic liquid 150 can be recycled to the hydrocarbon conversion zone 115.

The hydrocarbon conversion conditions depend on the particular hydrocarbon conversion process. The reaction temperature is typically in the range of about −20° C. to about 250° C. The pressure is typically in the range of about 0 MPa(g) to about 13.8 MPa(g).

Most hydrocarbon conversion reactions in ionic liquids are biphasic and take place at the interface in the liquid state due to the low solubility of hydrocarbons in ionic liquids.

The reaction will proceed simply by contacting the hydrocarbon feed and the liquid catalyst. In some instances, the reaction rate may be too slow to be commercially viable. When mass transfer rate is controlling, the reaction rate can be substantially increased by increasing the mixing intensity of hydrocarbon feed and liquid catalyst. After a certain point, increasing the mixing intensity will not provide any additional benefit. Mixing intensity can be controlled using pumps, flow configurations, and baffles. Baffles help to prevent a vortex from forming in the reactor, which would reduce the amount of mixing.

The contacting step may be practiced in laboratory scale experiments through full scale commercial operations. The process may be operated in batch, continuous, or semi-continuous mode. The contacting step can take place in various ways, with both countercurrent and co-current flow processes being suitable.

The reaction time is a function of the degree of mixing, the reaction temperature, and the mass/volume ratio of liquid catalyst to hydrocarbon being reacted. Generally, increasing any of these conditions will increase the reaction rate.

If a Brønsted acid is used without the addition of a metal halide in making the lactamium based ionic liquids as discussed below, it may be necessary to add an excess of the Brønsted acid used in the lactamium based ionic liquid or another strong Brønsted acid, for example, triflic acid or sulfuric acid, to the reaction zone.

Suitable lactamium based ionic liquids are described in U.S. application Ser. No. 14/271,308, entitled Synthesis of Lactam Based Ionic Liquids, filed May 6, 2014, and U.S. application Ser. No. 14/271,319, entitled Synthesis of N-Alkyl Lactam Based Ionic Liquids, filed May 6, 2014, each of which is incorporated herein by reference.

The ionic liquids have a lactamium based cation. One type of lactamium based ionic liquid catalyst has the general formula:

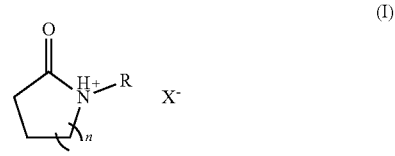

(I)

wherein R is hydrogen, an alkyl group having from 1 to 12 carbon atoms, an amine, an ether, or a silyl group, n is 1 to 8, and X⁻ is an anion group of a Brønsted acid HX or a halometallate.

In some embodiments, when R is hydrogen, X⁻ is p-toluenesulfonate, halide, or halometallate.

In one embodiment, when n is 3, X⁻ is p-toluenesulfonate, and R is an alkyl group, the alkyl group has from 1 to 5 carbon atoms.

In one embodiment, when n is 3, X⁻ is not a zinc halometallate.

Another way to represent this compound is:

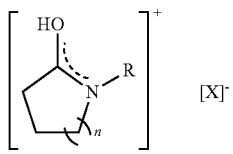

wherein R is hydrogen, an alkyl group having from 1 to 12 carbon atoms, an amine, an ether, or a silyl group, n is 1 to 8, and X⁻ is an anion group of a Brønsted acid HX or a halometallate.

Formula (I) is intended to cover both representations.

Another type of lactamium based ionic liquid has the general formula:

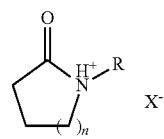

wherein the ring has at least one C=C double bond, R is hydrogen, an alkyl group having from 1 to 12 carbon atoms, an amine, an ether, or a silyl group, n is 1 to 8, and X⁻ is an anion group of a Brønsted acid HX or a halometallate.

The ring has at least one double bond. Larger rings may have more than one double bond. The double bond can be between any two adjacent carbons capable of forming a double bond.

Another way to represent this compound is

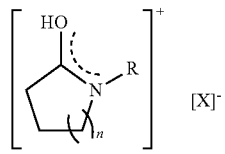

wherein the ring has at least one C=C double bond, R is hydrogen, an alkyl group having from 1 to 12 carbon atoms, an amine, an ether, or a silyl group, n is 1 to 8, and X⁻ is an anion group of a Brønsted acid HX or a halometallate.

Formula (II) is intended to cover both representations.

Examples of Formula (II) ionic liquids include, but are not limited to, 1,5-dihydro-pyrrol-2-one ionic liquids, 1,5-dihydro-1-methyl-2H-pyrrol-2-one based ionic liquids, 1,3-dihydro-2H-pyrrol-one ionic liquids, and 1,3-dihydro-1-methyl-2H-pyrrol-2-one based ionic liquids.

Another type of lactamium based ionic liquid has the general formula:

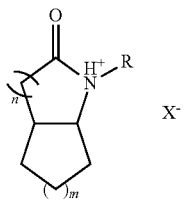

wherein R is hydrogen, an alkyl group having from 1 to 12 carbon atoms, an amine, an ether, or a silyl group, n is 1 to 8, m is 1 to 8, X⁻ is an anion group of a Brønsted acid HX or a halometallate, and the rings can be saturated or unsaturated.

The heterocyclic ring (ring with n) can be saturated or unsaturated. The hydrocarbon ring (ring with m) can be saturated, unsaturated, or aromatic. If the ring is unsaturated, the C=C double bond can be between any two adjacent carbons capable of forming a double bond. There can be one or more C=C double bonds in either ring or in both rings.

Another way to represent this compound is

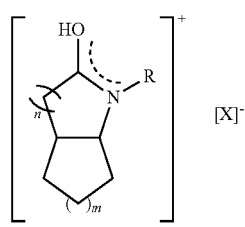

wherein R is hydrogen, an alkyl group having from 1 to 12 carbon atoms, an amine, an ether, or a silyl group, n is 1 to 8, m is 1 to 8, X⁻ is an anion group of a Brønsted acid HX or a halometallate, and the rings can be saturated or unsaturated.

Formula (III) is intended to cover both representations.

Examples of Formula (III) ionic liquids include, but are not limited to, octahydro-2H-indol-2-one ionic liquids, octahydro-1-methyl-2H-indol-2-one based ionic liquids, and 2-oxindole ionic liquids, and 1,3-dihydro-1-methyl-2H-indol-2-one based ionic liquids.

Suitable X⁻ groups include, but are not limited to, carboxylates, nitrates, phosphates, phosphinates, phosphonates, imides, cyanates, borates, sulfates (including bisulfates), sulfonates (including fluoroalkanesulfonates), acetates, halides, halometallates, and combinations thereof. Examples of X⁻ groups include, but are not limited to, following tetrafluoroborate, triflate, trifluoroacetate, chloroacetate, nitrate, hydrogen sulfate, hydrogen phosphate, dicyanoimide, methylsulfonate, and combinations thereof. Suitable halides include, but are not limited to, bromide, chloride, and iodide. Halometallates are mixtures of halides, such as bromide, chloride, and iodide, and metals. Suitable metals include, but are not limited to, Sn, Al, Zn, Mn, Fe, Ga, Cu, Ni, and Co. In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_3Br^-$, $Al_2Cl_6Br^-$, $Al_3Cl_9Br^-$, $AlBr_4^-$, $Al_3GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

In some embodiments when making a halometallate, the lactam compound is reacted with a Brønsted acid HX, such as HCl, where X is a halide to form a lactamium halide. The lactamium halide is then reacted with a metal halide to form the lactamium halometallate.

As is understood by those of skill in the art, the particular Brønsted acid used will depend on the anion desired. Suitable Brønsted acids include for example, sulfuric acid, p-toluenesulfonic acid, hydrochloric acid, hydrobromic acid, nitric acid, phosphoric acid, tetrafluoroboric acid, triflic acid, trifluoroacetic acid, chloroacetic acid, and methanesulfonic acid.

The lactamium based ionic liquid catalyst comprises at least one of:

a reaction product of a lactam compound having a general formula

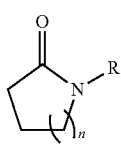
(IV)

wherein R is hydrogen, an alkyl group having from 1 to 12 carbon atoms, an amine, an ether, or a silyl group, n is 1 to 8;
and a Brønsted acid HX; or a Brønsted acid HX, where X is a halide, and a metal halide;
or a reaction product of a lactam compound having a general formula

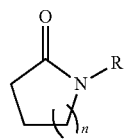
(V)

wherein the ring has at least one C=C double bond, R is hydrogen, an alkyl group having from 1 to 12 carbon atoms, an amine, an ether, or a silyl group, n is 1 to 8;
and a Brønsted acid HX; or a Brønsted acid HX, where X is a halide, and a metal halide;
or a reaction product of a lactam compound having a general formula

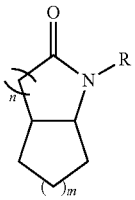
(VI)

wherein R is hydrogen, an alkyl group having from 1 to 12 carbon atoms, an amine, an ether, or a silyl group, n is 1 to 8, m is 1 to 8, and the rings can be saturated or unsaturated;
and a Brønsted acid HX; or a Brønsted acid HX, where X is a halide, and a metal halide.

A lactamium based ionic liquid can be made by reacting a lactam compound having a general formula

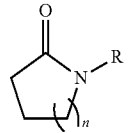
(IV)

wherein R is hydrogen, an alkyl group having from 1 to 12 carbon atoms, an amine, an ether, or a silyl group, and n is 1 to 8;
with a Brønsted acid HX; or a Brønsted acid HX, where X is a halide, and a metal halide.

Another lactamium based ionic liquid can be made by reacting a lactam compound having a general formula

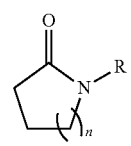
(V)

wherein the ring has at least one C=C double bond, R is hydrogen, an alkyl group having from 1 to 12 carbon atoms, an amine, an ether, or a silyl group, and n is 1 to 8;
with a Brønsted acid HX; or a Brønsted acid HX, where X is a halide, and a metal halide.

Another lactamium based ionic liquid can be made by reacting a lactam compound having a general formula

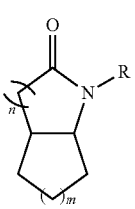
(VI)

wherein R is hydrogen, an alkyl group having from 1 to 12 carbon atoms, an amine, an ether, or a silyl group, n is 1 to 8, and m is 1 to 8, and the rings can be saturated or unsaturated;
with a Brønsted acid HX; or a Brønsted acid HX, where X is a halide, and a metal halide.

The heterocyclic ring (ring with n) can be saturated or unsaturated. The hydrocarbon ring (ring with m) can be saturated, unsaturated, or aromatic. If the ring is unsaturated, the C=C double bond can be between any two adjacent carbons capable of forming a double bond. There can be one or more C=C double bonds in either ring or in both rings.

The reaction can take place at temperatures in the range of about −36° C. to the decomposition temperature of the ionic liquid, or about −20° C. to less than the decomposition temperature of the ionic liquid, or about 0° C. to about 200° C., or about 0° C. to about 150° C., or about 0° C. to about 120° C., or about 20° C. to about 80° C.

The reaction typically takes place at atmospheric pressure, although higher or lower pressures could be used if desired.

When making halometallate compounds, the reaction can take place in an inert atmosphere.

The reaction typically takes about 1 min to multiple days, depending on the ionic liquid. Those made with the Brønsted acid typically take minutes to hours, while the halometallates typically take minutes to one or more days.

The reaction may be practiced in laboratory scale experiments through full scale commercial operations. The process may be operated in batch, continuous, or semi-continuous mode.

In some embodiments, the reaction can take place in the absence of a solvent. In other embodiments, it can take place in the presence of a solvent. The contacting can take place in the presence of one or more solvents. Suitable solvents for non-halometallate ionic liquids include, but are not limited to water, toluene, dichloromethane, liquid carboxylic acids such as acetic acid or propanoic acid, alcohols, such as methanol and ethanol, and combinations thereof. When water is used as the solvent, an additional product may form. The products can be separated using known separation techniques. Non-protic solvents, such as dichloromethane, are suitable for use with halometallates.

The ratio of the Brønsted acid to the lactam compound is about 1:1 to about 3:1. In some embodiments, when making a halometallate from the lactamium halide using a Brønsted acid, the ratio of Brønsted acid to the lactam compound is about 1:1.

Alkylation

The alkylation reaction using the lactamium based ionic liquid is carried out at mild temperatures, and is typically a two-phase reaction. In some embodiments, cooling may be needed. If cooling is needed, it can be provided using any known methods. The catalyst effects the alkylation of the paraffin and the olefin.

Typical alkylation reaction conditions include a temperature in the range of about −20° C. to the decomposition temperature of the ionic liquid, or about −20° C. to about 100° C., or about −20° C. to about 80° C., or about 0° C. to about 80° C., or about 20° C. to about 80° C. It is preferred to have an ionic liquid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 1 min to about 60 min, or about 5 min to about 60 min.

The acidity needs to be controlled to provide for suitable alkylation conditions. This can be done with an acid or acid precursor, such as HCl, 2-chlorobutane, or tert-butyl chloride, for example. Alternatively, the excess acid could be stripped from the fresh ionic liquid with, for example, isobutane, nitrogen, or triethylsilane (TES), and the acid level could be controlled at the low level needed during the reaction. Another alternative is to reduce the pressure and add heat to remove the excess acid.

The paraffin and olefin can be introduced separately or as a mixture. The molar ratio between the paraffin and the olefin is in the range between 100:1 and 1:1, or 50:1 and 2:1, or 20:1 and 2:1.

In a semi-batch system, the paraffin is introduced first, then the olefin is added, or a mixture of isoparaffin and olefin can be introduced. The catalyst is measured in the reactor with respect to the amount of olefins, with a catalyst to olefin weight ratio between 0.1 and 10, or 0.2 and 5, or 0.5 and 2.

The heat generated by the reaction can be eliminated using any of the means known to the skilled person.

At the reactor outlet, the hydrocarbon phase is separated from the ionic liquid phase by gravity settling based on density differences, or by other separation techniques known to those skilled in the art. The hydrocarbons are separated by distillation, and the starting isoparaffin which has not been converted is recycled to the reactor.

Typical alkylation conditions may include a catalyst volume in the reactor of from 1 vol % to 50 vol %, a temperature of from 0° C. to 100° C., a pressure of from 300 kPa to 2500 kPa, an isobutane to olefin molar ratio of from 2 to 20 and a residence time of 1 min to 1 hour.

The paraffin used in the alkylation process preferably comprises a paraffin having from 2 to 10 carbon atoms, or 4 to 8 carbon atoms, or 4 to 5 carbon atoms. The olefin used in the alkylation process preferably has from 2 to 10 carbon atoms, 3 to 8 carbon atoms, or 3 to 5 carbon atoms. One application of the process is to upgrade low value $C_4$ hydrocarbons to higher value alkylates.

To that extent, one specific embodiment is the alkylation of butanes with butylenes to generate $C_8$ compounds. Preferred products include trimethylpentane (TMP), and while other $C_8$ isomers are produced, one competing isomer is dimethylhexane (DMH). The quality of the product stream can be measured in the ratio of TMP to DMH, with a high ratio desired.

In another embodiment, the invention comprises passing an isoparaffin and an olefin to an alkylation reactor, where the alkylation reactor includes an ionic liquid catalyst to react the olefin with the isoparaffin to generate an alkylate. The isoparaffin has from 4 to 10 carbon atoms, and the olefin has from 2 to 10 carbon atoms.

Oligomerization

Oligomerization reaction zones in general are maintained at conditions that may vary widely. Suitable hydrocarbon feed for isomerization reactions includes $C_2$ to $C_{23}$ olefins. The temperature of the oligomerization reaction zones of the present invention in which a resin catalyst is used is typically about −20° C. to about 250° C., or 50° C. to about 200° C., or 50° C. to about 150° C. Pressures in the oligomerization zone using the ionic liquid catalyst will be sufficient to maintain the liquid phase in and out of the reactor, typically about 0.3 MPa(g) to about 6.9 MPa(g) (50 to 1000 psig), or about 0.3 MPa(g) to about 3.4 MPa(g) (50 to 500 psig), or about 1.4 MPa(g) to about 2.4 MPa(g) (200 to 350 psig), or about 2.4 MPa(g) to about 6.9 MPa(g) (350 to 1000 psig). Oligomerization conditions may also include a liquid hourly space velocity (LHSV) of about 0.5 to about 8 hr', or about 1 to about 6 $hr^{-1}$.

Isomerization

Suitable hydrocarbon feed for isomerization reactions includes $C_2$ to $C_{23}$ paraffins.

Suitable reaction conditions include a temperature up to the decomposition temperature of the ionic liquid, typically of about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa(g) to about 13.8 MPa(g), or about 0 MPa(g) to about 8.1 MPa(g), or about 0 MPa(g) to about 5 MPa(g), or about 0 MPa(g) to about 3.5 MPa(g). The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The reaction can take place in the presence of an added acid or acid precursor. Suitable acids or acid precursors include, but are not limited to, HCl, 2-chlorobutane, or tert-butyl chloride, for example.

The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. The reaction time is a function of the degree of mixing, the reaction temperature, the concentration of acid and the mass/volume ratio of liquid catalyst to hydrocarbon being reacted. Generally, increasing any of these conditions will increase the reaction rate.

Isomerization processes utilizing ionic liquid catalysts were described in application Ser. No. 13/931,765, entitled CATALYTIC ISOMERIZATION OF PARAFFINS USING IONIC LIQUID, filed Jun. 28, 2013; Application Ser. No. 13/931,770, entitled CATALYTIC ISOMERIZATION OF HEPTANE USING IONIC LIQUID, filed Jun. 28, 2013; Application Ser. No. 13/931,776, entitled CATALYTIC ISOMERIZATION OF PENTANE USING IONIC LIQUID, filed Jun. 28, 2013; each of which is incorporated herein by reference.

Disproportionation

Suitable hydrocarbon feeds for disproportionation reactions include $C_2$ to $C_{23}$ paraffins. Feeds comprising two or more paraffins are also acceptable.

Suitable reaction conditions include a temperature of about less than the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 20.7 MPa, or about 0 MPa to about 8.1 MPa, or about 0 MPa to about 5 MPa, or about 0 MPa to about 3.5 MPa. The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The reaction can take place in the presence of an added acid or acid precursor. Suitable acids or acid precursors include, but are not limited to, HCl, 2-chlorobutane, or tert-butyl chloride, for example. The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. The reaction time is a function of the degree of mixing, the reaction temperature, the concentration of acid and the mass/volume ratio of liquid catalyst to hydrocarbon being reacted. Generally, increasing any of these conditions will increase the reaction rate.

Disproportionation processes using ionic liquids were described in application Ser. No. 13/931,780, entitled CATALYTIC DISPROPORTIONATION OF PARAFFINS USING IONIC LIQUID, filed Jun. 28, 2013; Application Ser. No. 13/931,783, entitled CATALYTIC DISPROPORTIONATION OF HEPTANE USING IONIC LIQUID, filed Jun. 28, 2013; and application Ser. No. 13/931,789, entitled CATALYTIC DISPROPORTIONATION OF PENTANE USING IONIC LIQUID, filed Jun. 28, 2013; each of which is incorporated herein by reference.

Reverse Disproportionation

The microscopic reverse of pentane disproportionation is the combination of one mole of hexane and one mole of butane to form two moles of pentane. This type of reaction is referred to herein as reverse disproportionation. Reverse disproportionation-type reactions can occur in which two paraffins having different carbon numbers react to form two different paraffins having different carbon numbers from those of the feed where the total number of moles of product and moles of carbon and hydrogen in the products does not change from the total number in the feed (e.g., pentane and octane reacting to form hexane and heptane). Utilizing the equilibrium among the various species, the concentration of the product can be controlled by varying the relative ratios of the species. Consequently, two different paraffinic feed sources of varying carbon count can be reacted to obtain a product containing paraffins of intermediate carbon count.

More generally, this process involves the net transfer of $CH_2$ units between paraffins, where $CH_2$ unit refers to the transfer of 1 C and 2 H, not necessarily a methylene unit. The products result from the donation and acceptance of net $CH_2$ units to and from various paraffins. Thus, two paraffinic feeds having different carbon counts can be reacted to produce a product having an intermediate carbon count. For example, the reaction of butane with a larger paraffin, e.g., $Cl_6$, produces a product containing paraffins in the $C_5$ to Cis range.

In addition to the net $CH_2$ transfer, the process favors the formation of branched paraffins, which are more valuable than normal paraffins because they have more desirable octane numbers and cloud points.

Typically, hydrocarbons having a carbon number from 1-200 or more can be selected as feeds for the process. Depending on the desired product, one or two (or more) hydrocarbon feeds could be selected.

In some embodiments involving reverse disproportion, one larger and one smaller paraffin feed can be used to produce a product composition having an intermediate carbon count. The smaller feed typically has carbon numbers ranging from 1-198, and the larger feed typically has carbon numbers ranging from 3-200. There is generally a difference of at least 2 or more carbon numbers between the two feeds, or at least 3, or at least 4, or at least 5, or at least 6 or more. In some embodiments involving reverse disproportionation, the reaction mixture has an amount of at least one of the intermediate products equal to or in excess of the amount formed by the disproportionation reaction of either feed alone.

In some embodiments, the smaller feed typically has carbon numbers ranging from 4-23, and the larger feed typically has carbon numbers ranging from 6-25. There is generally a difference of at least 2 or more carbon numbers between the two feeds, or at least 3, or at least 4, or at least 5, or at least 6 or more.

The liquid hydrocarbon feed is contacted with the liquid catalyst at temperatures of in the range of about −20° C. to the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 20.7 MPa, or about 0 MPa to about 8.1 MPa. In some embodiments, the pressure should be sufficient to ensure that the hydrocarbon feed is in a liquid state. Small amounts of vapor may also be present, but this should be minimized. In other embodiments, using propane and other light paraffins, the temperatures may not allow for a liquid state. In this case, a gas phase or a supercritical phase can be used. The reaction typically takes places in the presence of a gas. Suitable gases include, but are not limited to nitrogen, hydrogen, argon, helium, hydrogen chloride and the like.

The reaction can take place in the presence of an added acid or acid precursor. Suitable acids or acid precursors include, but are not limited to, HCl, 2-chlorobutane, or tert-butyl chloride, for example.

The residence time in the reaction zone is generally less than about 10 hr, or less than 7 hr, or less than 5 hr, or less than 4 hr, or less than 3 hr, or less than 2 hr, or less than 1 hr. The reaction time is a function of the degree of mixing, the reaction temperature, the concentration of acid and the mass/volume ratio of liquid catalyst to hydrocarbon being reacted. Generally, increasing any of these conditions will increase the reaction rate.

Reverse disproportionation processes using ionic liquids were described in Application Ser. No. 61/841,263, entitled CATALYTIC REVERSE DISPROPORTIONATION OF PARAFFINS USING IONIC LIQUID, filed Jun. 28, 2013, and application Ser. No. 14/303,586, entitled CATALYTIC REVERSE DISPROPORTIONATION OF PARAFFINS USING IONIC LIQUID, filed Jun. 12, 2014, each of which is incorporated herein by reference.

By the term "about," we mean within 10% of the value, or within 5%, or within 1%.

EXAMPLES

Example 1

Preparation of Caprolactamium Chloride

In a 100 mL round bottom flask, an HCl solution (24.84 g, 0.22 mol) was added to a toluene solution of caprolactam (25.05 g, 0.22 mol). After stirring for 2 hours at room temperature, the volatiles were removed. Yield: 34.2 g. The solid was dissolved in dichloromethane, filtered, and volatiles were removed. $^1$H NMR (500 MHz, d$_6$-DMSO): 1.49-1.64 (m, 6H), 2.35 (t, 2H), 3.08 (t, 2H), 7.90 (broad s). $^{13}$C NMR (125 MHz, d$_6$-DMSO): 23.31, 29.78, 30.40, 36.16, 42.25, 178.90.

Example 2

Preparation of Caprolactamium Chloroaluminate

All procedures were performed in a nitrogen glovebox. In a vial containing caprolactamium chloride (3.48 g, 0.23 mol), aluminum trichloride (6.37 g, 0.47 mol) was added slowly while stirring the mixture. After stirring for 5 hours, the mixture was allowed to settle and liquid was decanted. $^1$H NMR (500 MHz, CDCl$_3$): 1.85-1.94 (m, 6H), 2.90 (t, 2H), 3.63 (q, 2H), 8.07 (broad s). $^{13}$C NMR (125 MHz, CDCl$_3$): 23.31, 29.78, 30.40, 36.18, 42.24, 178.90.

Example 3

Alkylation of Isobutane with 2-Butene Using Caprolactamium Chloroaluminate Ionic Liquid Catalyst In a N$_2$ atmosphere, caprolactamium chloroaluminate (8 g) was loaded into a 300 ml autoclave containing a baffle. Prior to loading, the autoclave and baffle had been dried for several hours above 100° C. The autoclave was charged with 80 g isobutane and pressurized with 3.4 MPa(g) (500 psig) of nitrogen. The contents were stirred at 1500 rpm, and 8 g 2-butene was added over time (about 7.79 mL/h) at room temperature. After 2 hr, the reaction mixture was allowed to settle and the liquid product was sampled directly from the autoclave. The sample was passed through a silica column then analyzed by gas chromatography. The results are shown in Table 1. (The groupings below include all isomers having the same carbon number.) The % butenes conversion was calculated using 100—(the weight of butenes in the product divided by the weight of butenes added). RONC is the Research Octane Number Calculated. TMP/DMH is the weight ratio of trimethylpentanes to dimethylhexanes in the product. The % Selectivity is (wt % of that paraffin)/(sum of wt % of the C5 and larger products formed).

TABLE 1

|  | Caprolactamium Chloroaluminate |
|---|---|
| Butenes Conversion | 100 |
| RONC | 87 |
| TMP/DMH | 3.0 |
| % Sel. C5 Paraffins | 16 |
| % Sel. C6 Paraffins | 8 |
| % Sel. C7 Paraffins | 6 |
| % Sel. C8s, incld unknown | 58 |
| % Sel. C9s | 12 |
| % Sel. C5-C7s | 30 |

Example 4

Alkylation of Isobutane with 2-Butene Using Caprolactamium Chloroaluminate Ionic Liquid Catalyst In a N$_2$ atmosphere, caprolactamium chloroaluminate was loaded into a 300 ml autoclave containing a baffle. Prior to loading, the autoclave and baffle had been dried for several hours above 100° C. The number of acid sites in the ionic liquid was adjusted to optimize the performance. The autoclave was charged with 80 g isobutane and pressurized with 3.4 MPa(g) (500 psig) of nitrogen. The contents were stirred at 1500 rpm, and 8 g 2-butene was added over time (about 7.79 mL/h) at room temperature. After 2 hr, the reaction mixture was allowed to settle and the liquid product was sampled directly from the autoclave. The sample was passed through a silica column then analyzed by gas chromatography. The preparation of the caprolactamium chloroaluminate of Batch 1 followed the description given above in Examples 1 and 2, except the isolated solid was not washed with dichloromethane and filtered as in Example 1. Also, after the addition of the aluminum trichloride in Example 2, the reaction mixture of Batch 1 was heated using a hot plate until stirring was improved. The preparation of the caprolactamium chloroaluminate of Batch 2 followed the description given in Examples 1 and 2. The results are shown in Table 2. (The groupings below include all isomers having the same carbon number.) The % butenes conversion was calculated using 100—(the weight of butenes in the product divided by the weight of butenes added). RONC is the Research Octane Number Calculated. TMP/DMH is the weight ratio of trimethylpentanes to dimethylhexanes in the product. The % Selectivity is (wt % of that paraffin)/(sum of wt % of the $C_5$ and larger products formed).

TABLE 2

|  | Batch 1 | Batch 1 | Batch 1 | Batch 2 | Batch 2 + 0.083 g t-BuCl |
|---|---|---|---|---|---|
| IL mass (g) | 8 | 4 | 1 | 1 | 1 |
| Butenes Conversion | 100 | 100 | 98 | 79 | 99 |
| RONC | 91 | 92 | 94 | 93 | 93 |
| TMP/DMH | 5.5 | 9.3 | 13 | 13 | 12 |
| % Sel. C8s, incld unknown | 70 | 77 | 76 | 72 | 73 |
| % Sel. C9s | 11 | 13 | 15 | 19 | 13 |
| % Sel. C5-C7s | 19 | 10 | 9 | 9 | 13 |

Example 5

Isomerization and Disproportionation of n-Hexane Using Caprolactamium Chloroaluminate Ionic Liquid Catalyst In a $N_2$ atmosphere, caprolactamium chloroaluminate (4 g) was loaded into a 75 ml Hastelloy C autoclave that had been dried at 110° C. for several hours. After loading the ionic liquid into the autoclave, n-hexane (8 g) and tert-butyl chloride (0.42 g) were added. The ionic liquid to hydrocarbon weight ratio was 1:2, and the tert-butyl chloride to ionic liquid molar ratio was 1:2. The autoclave was heated to 95° C. with stirring (600 rpm). After 4.25 hr, the autoclave was cooled, and the hydrocarbon phase was separated from the ionic liquid. The hydrocarbon phase was analyzed by gas chromatography using the ASTM UOP690-99 method. The results are shown in Tables 3 and 4. (The groupings below include all isomers having the same carbon number.) The % $nC_6$ conversion was calculated using the wt % of $nC_6$ as determined by gas chromatography.

TABLE 3

| % nC6 Conv. | time (h) | C3-P | C4P | C5P | C6P | C7P | C8P | C8 + N | Sum |
|---|---|---|---|---|---|---|---|---|---|
| 46.5 | 4.25 | 0.1 | 15.4 | 18.5 | 53.5 | 7.0 | 1.5 | 2.1 | 98.1 |

TABLE 4

| Paraffin | Wt % in product | % isoparaffin | % normal paraffin |
|---|---|---|---|
| C4P | 15 | 90 | 10 |
| C5P | 19 | 86 | 14 |
| C6P | 53 | 34 | 66 |

Example 6

Reverse Disproportionation of n-Butane and n-Heptane Using Caprolactamium Chloroaluminate Ionic Liquid Catalyst A 300 mL Hastelloy C autoclave, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. Caprolactamium chloroaluminate (30 g) was loaded into the 300 ml Hastelloy C autoclave in a $N_2$ atmosphere. tert-Butyl chloride (3.39 g) and heptane (12 g) were loaded into the 75 mL stainless steel sample cylinder in a $N_2$ atmosphere. Outside the glovebox, the autoclave was charged with butane (114 g). The autoclave was heated to 100° C. with gentle stirring (~100 rpm). Once the autoclave reached 100° C., stirring was stopped and the contents of the sample cylinder were added to the autoclave with an overpressure of nitrogen. Upon complete addition, the stir rate was increased to 1700 rpm. Samples were taken during the experiment and analyzed by gas chromatography. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was the ASTM UOP690-99 method. The results are shown in Table 5. (The groupings below include all isomers having the same carbon number.) The % $nC_7$ conversion was calculated using the wt % of $nC_7$ as determined by gas chromatography.

TABLE 5

| Time (h) | % nC7 Conv. | C3P | C4P | C5P | C6P | C7P | C8P | nC9 | C9+ |
|---|---|---|---|---|---|---|---|---|---|
| 0 | 0 | 0 | 90.2 | 0 | 0 | 9.8 | 0 | 0 | 0 |
| 0.1 | 81.3 | 1.0 | 85.7 | 8.6 | 1.7 | 1.8 | 0.3 | 0.0 | 0.1 |
| 2.75 | 95.1 | 3.0 | 77.0 | 15.6 | 2.8 | 0.5 | 0.2 | 0.0 | 0.0 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A hydrocarbon conversion process comprising:
contacting a hydrocarbon feed with a lactamium based ionic liquid catalyst in a hydrocarbon conversion zone under hydrocarbon conversion conditions to form a mixture comprising reaction products, and the lactamium based ionic liquid catalyst.

2. The process of claim 1 wherein the lactamium based ionic liquid catalyst comprises at least one of:
a reaction product of a lactam compound having a general formula

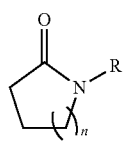

(IV)

wherein R is hydrogen, an alkyl group having from 1 to 12 carbon atoms, an amine, an ether, or a silyl group, n is 1 to 8;
and a Brønsted acid HX; or a Brønsted acid HX, where X is a halide, and a metal halide;
or
a reaction product of a lactam compound having a general formula

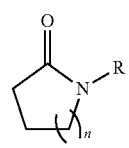

(V)

wherein the ring has at least one C═C double bond, R is hydrogen, an alkyl group having from 1 to 12 carbon atoms, an amine, an ether, or a silyl group, n is 1 to 8;
and a Brønsted acid HX; or a Brønsted acid HX, where X is a halide, and a metal halide;
or
a reaction product of a lactam compound having a general formula

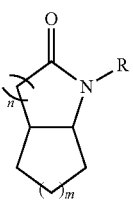

(VI)

wherein R is hydrogen, an alkyl group having from 1 to 12 carbon atoms, an amine, an ether, or a silyl group, n is 1 to 8, m is 1 to 8, and the rings can be saturated or unsaturated;
and a Brønsted acid HX; or a Brønsted acid HX where X is a halide, and a metal halide.

3. The process of claim 2 wherein an anion of the Brønsted acid HX is at least one of carboxylates, nitrates, phosphates, phosphinates, phosphonates, imides, cyanates, borates, sulfates, sulfonates, acetates, and halides.

4. The process of claim 2 wherein the ionic liquid has the general formula (III) and wherein at least one ring has at least one C═C double bond.

5. The process of claim 1 wherein the hydrocarbon conversion process comprises at least one of alkylation, oligomerization, isomerization, disproportionation, and reverse disproportionation.

6. The process of claim 1 wherein the hydrocarbon conversion conditions include at least one of a temperature in a range of about −20° C. to about 250° C., and a pressure in a range of about 0 MPa(g) to about 7.1 MPa(g).

7. The process of claim 1 further comprising separating the reaction products from the lactamium based ionic liquid catalyst.

8. The process of claim 1 further comprising regenerating the lactamium based ionic liquid catalyst.

9. The process of claim 8 further comprising recycling the regenerated lactamium based ionic liquid to the hydrocarbon conversion zone.

10. The process of claim 1 further comprising adding an acid, or an acid precursor to the hydrocarbon conversion zone.

11. The process of claim 1 wherein the hydrocarbon conversion process comprises alkylation, the feed comprises $C_2$ to $C_{10}$ paraffins and olefins, and wherein the hydrocarbon conversion conditions include a catalyst volume in the reactor of from about 1 vol % to about 50 vol %, a temperature of from about 0° C. to about 100° C., a pressure from about 0.3 MPa(g) to about 2.5 MPa(g), an isobutane to olefin molar ratio from about 2 to about 20, and a residence time of about 1 min to about 1 hour.

12. The process of claim 1 wherein the hydrocarbon conversion process comprises oligomerization, the feed comprises $C_2$ to $C_{23}$ olefins, and wherein the hydrocarbon conversion conditions include a temperature of about 50° C. to about 200° C., a pressure of about 0.3 MPa(g) to about 3.4 MPa(g), and a liquid hourly space velocity of about 0.5 to about 8 $hr^{-1}$.

13. The process of claim 1 wherein the hydrocarbon conversion process comprises at least one of isomerization, and disproportionation, the feed comprises $C_2$ to $C_{23}$ paraffins, and wherein the hydrocarbon conversion conditions include a temperature of about 0° C. to about 200° C., a pressure of about 0 MPa(g) to about 20.7 MPa(g), and a residence time of less than about 12 hour.

14. The process of claim 1 wherein the hydrocarbon conversion process comprises reverse disproportionation, the feed comprises $C_4$ to $C_{25}$ paraffins, and wherein the hydrocarbon conversion conditions include a temperature of about 0° C. to about 250° C., a pressure of about 0 MPa(g) to about 20.7 MPa(g), and a residence time of less than about 12 hour.

15. A hydrocarbon conversion process comprising:
contacting a hydrocarbon feed with a lactamium based ionic liquid catalyst in a hydrocarbon conversion zone under hydrocarbon conversion conditions to form a mixture comprising conversion reaction products, and the lactamium based ionic liquid catalyst, wherein the hydrocarbon conversion processes comprises at least one of alkylation, oligomerization, isomerization, disproportionation, and reverse disproportionation;
separating the conversion reaction products from the lactamium based ionic liquid catalyst;
recovering the conversion reaction products; and
recycling the lactamium based ionic liquid to the reaction zone;

wherein the lactamium based ionic liquid catalyst comprises at least one of:

a reaction product of a lactam compound having a general formula

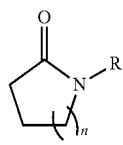

(IV)

wherein R is hydrogen, an alkyl group having from 1 to 12 carbon atoms, an amine, an ether, or a silyl group, n is 1 to 8;
and a Brønsted acid HX; or a Brønsted acid HX, where X is a halide, and a metal halide;
or
a reaction product of a lactam compound having a general formula

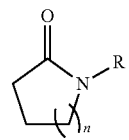

(V)

wherein the ring has at least one C≡C double bond, R is hydrogen, an alkyl group having from 1 to 12 carbon atoms, an amine, an ether, or a silyl group, n is 1 to 8;
and a Brønsted acid HX; or a Brønsted acid HX, where X is a halide, and a metal halide;
or
a reaction product of a lactam compound having a general formula

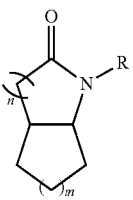

(VI)

wherein R is hydrogen, an alkyl group having from 1 to 12 carbon atoms, an amine, an ether, or a silyl group, n is 1 to 8, m is 1 to 8, and the rings can be saturated or unsaturated;
and a Brønsted acid HX; or a Brønsted acid HX, where X is a halide, and a metal halide.

16. The process of claim 15 wherein an anion of the Brønsted acid HX is at least one of carboxylates, nitrates, phosphates, phosphinates, phosphonates, imides, cyanates, borates, sulfates, sulfonates, acetates, and halides.

17. The process of claim 15 wherein the hydrocarbon conversion conditions include at least one of a temperature in a range of about −20° C. to about 250° C., and a pressure in a range of about 0 MPa(g) to about 20.7 MPa(g).

18. The process of claim 15 further comprising regenerating the lactamium based ionic liquid catalyst before recycling the lactamium based ionic liquid to the reaction zone.

19. The process of claim 15 further comprising adding an acid, or an acid precursor to the reaction zone.

20. The process of claim 15 wherein the hydrocarbon conversion process comprises alkylation, the feed comprises $C_2$ to $C_{10}$ paraffins and olefins, and wherein the hydrocarbon conversion conditions include a catalyst volume in the reactor of from about 1 vol % to about 50 vol %, a temperature of from about 0° C. to about 100° C., a pressure from about 0.3 MPa(g) to about 2.5 MPa(g), an isobutane to olefin molar ratio from about 2 to about 20, and a residence time of about 1 min to about 1 hour; or wherein the hydrocarbon conversion process comprises oligomerization the feed comprises $C_2$ to $C_{23}$ olefins, and wherein the hydrocarbon conversion conditions include a temperature of about 50° C. to about 200° C., a pressure of about 0.3 MPa(g) to about 3.4 MPa(g), and a liquid hourly space velocity of about 0.5 to about 8 $hr^{-1}$; or wherein the hydrocarbon conversion process comprises at least one of isomerization, and disproportionation, the feed comprises $C_2$ to $C_{23}$ paraffins, and wherein the hydrocarbon conversion conditions include a temperature of about 0° C. to about 200° C., a pressure of about 0 MPa(g) to about 20.7 MPa(g), and a residence time of less than about 12 hour; or wherein the hydrocarbon conversion process comprises reverse disproportionation, the feed comprises $C_4$ to $C_{25}$ paraffins, and wherein the hydrocarbon conversion conditions include a temperature of about 0° C. to about 250° C., a pressure of about 0 MPa(g) to about 20.7 MPa(g), and a residence time of less than about 12 hour; or combinations thereof.

\* \* \* \* \*